United States Patent [19]

Worthington et al.

[11] Patent Number: 4,743,602

[45] Date of Patent: May 10, 1988

[54] THIOPHENE CYCLOPROPYL AMINE COMPOUNDS, COMPOSITIONS AND FUNGICIDAL USE

[75] Inventors: Paul A. Worthington; Vivienne M. Anthony, both of Maidenhead, England

[73] Assignee: Imperial Chemical Industries PLC, London, England

[21] Appl. No.: 69,603

[22] Filed: Jun. 30, 1987

[30] Foreign Application Priority Data

Jul. 16, 1986 [GB] United Kingdom ............... 8617378
Oct. 1, 1986 [GB] United Kingdom ............... 8623568

[51] Int. Cl.⁴ ............ C07D 333/20; C07D 413/08; A01N 43/10; A01N 43/84
[52] U.S. Cl. .................. 514/231.5; 514/252; 514/326; 514/422; 514/438; 514/445; 514/63; 514/227.8; 544/60; 544/69; 544/146; 544/229; 544/379; 546/14; 546/212; 546/213; 548/110; 548/527; 549/65; 549/74; 549/75; 549/491
[58] Field of Search ............ 544/60, 69, 146, 229, 544/379; 546/14, 212, 213; 548/110, 527, 63; 514/222, 230, 252, 326, 422, 438, 445; 549/65, 74, 75

[56] References Cited

U.S. PATENT DOCUMENTS 4,022,903 5/1977 Stein et al. .................... 514/438

FOREIGN PATENT DOCUMENTS 656134 1/1963 Canada.

Primary Examiner—Robert W. Ramsuer
Attorney, Agent, or Firm—Cushman, Darby & Cushman

[57] ABSTRACT

According to the invention there are provided compounds useful for combatting fungi having the general formula (I):

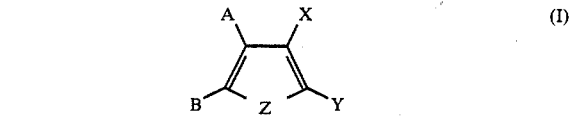

and stereoisomers thereof, wherein one of X and Y, but not both, is a group of the formula (II):

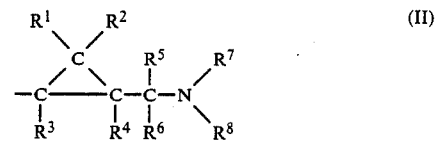

and the other of X and Y is a hydrogen atom, a halogen atom, or an alkyl, cycloalkyl, cycloalkylalkyl, alkenyl, alkynyl, aryl, aralkyl, alkoxy, aryloxy or haloalkyl group or a

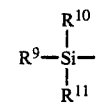

group wherein $R^9$, $R^{10}$ and $R^{11}$ can be alkyl, alkenyl, alkynyl, cycloalkyl, cycloalkylalkyl or aryl, Z is an oxygen atom, a sulphur atom or an —NH-group, A and B have the same significance as X or Y excluding a group of formula (II), $R^1$, $R^2$, $R^3$ and $R^4$ each represent a hydrogen atom, a halogen atom or an alkyl group containing from 1 to 4 carbon atoms, $R^5$ and $R^6$ each represent a hydrogen atom or an alkyl group containing from 1 to 4 carbon atoms, and $R^7$ and $R^8$ each represent an alkyl group containing from 1 to 4 carbon atoms or $R^7$ and $R^8$ together with the adjacent nitrogen atom form a heterocyclic ring which may optionally contain an additional hetero atom; and acid addition salts thereof.

7 Claims, No Drawings

THIOPHENE CYCLOPROPYL AMINE COMPOUNDS, COMPOSITIONS AND FUNGICIDAL USE

This invention relates to tertiary amine compounds containing a cyclopropane ring which are useful as fungicides, to a process for preparing the compounds, to fungicidal compositions containing them and to methods of using them to combat fungi, especially fungal infections in plants.

According to the invention there are provided compounds having the general formula (I):

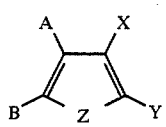   (I)

and stereoisomers thereof, wherein one of X and Y, but not both, is a group of the formula (II)

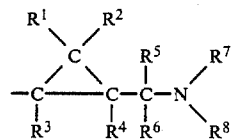   (II)

and the other of X and Y is a hydrogen atom, a halogen atom, or an alkyl, cycloalkyl, cycloalkylalkyl, alkenyl, alkynyl, aryl, aralkyl, alkoxy, aryloxy or haloalkyl group, or a

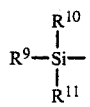

group wherein $R^9$, $R^{10}$ and $R^{11}$ can be alkyl, alkenyl, alkynyl, cycloalkyl, cycloalkylalkyl or aryl, Z is an oxygen atom, a sulphur atom or an —NH— group, A and B have the same significance as X or Y excluding a group of formula (II), $R^1$, $R^2$, $R^3$ and $R^4$ each represent a hydrogen atom, a halogen atom or an alkyl group containing from 1 to 4 carbon atoms, $R^5$ and $R^6$ each represent a hydrogen atom or an alkyl group containing from 1 to 4 carbon atoms, and $R^7$ and $R^8$ each represent an alkyl group containing from 1 to 4 carbon atoms or $R^7$ and $R^8$ together with the adjacent nitrogen atom form a heterocyclic ring which may optionally contain an additional hetero atom; and acid addition salts thereof.

The compounds of the invention are generally obtained in the form of mixtures of geometric isomers. However, these and other mixtures of optical isomers can be separated into individual isomers by methods in the art and such isomers constitute a part of the present invention.

When $R^7$ and $R^8$, together with the adjacent N-atom, represent a heterocyclic ring this may be, for example, a piperidine, morpholine, thiomorpholine, pyrrolidine or piperazine ring and any of these rings may bear substituents such as one or more $C_{1-4}$ alkyl groups or a phenyl group, or a hydroxy$C_{1-4}$alkyl group.

Alkyl groups containing from 1 to 4 carbon atoms represented by $R^1$ to $R^8$ may be either straight or branched chain groups, for example methyl, ethyl, n-propyl, iso-propyl, n-butyl, sec-butyl, iso-butyl or tert-butyl. Alkyl and alkoxy groups represented by A, B, X or Y may be straight or branched chain groups containing from 1 to 6 carbon atoms; cycloalkyl groups represented by A, B, X or Y may be cyclopropyl, cyclobutyl, cyclopentyl or cyclohexyl groups.

The halogen atoms which $R^1$ to $R^4$, A, B, X or Y may represent may be fluorine, chlorine or bromine.

Alkenyl and alkynyl groups represented by A, B, X or Y may contain from 2 to 6 carbon atoms.

Examples of A, B, X or Y when these are aryl, aralkyl, aryloxy or aralkoxy groups are phenyl, benzyl, phenoxy and benzyloxy. These rings may be substituted with one or more atoms halogen (eg. fluorine, chlorine or bromine), or $C_{1-6}$ alkyl [eg. methyl, ethyl, propyl (n- or iso-propyl) and butyl (n-, sec-, iso, or t-butyl)], $C_{1-6}$ alkoxy (eg. methoxy, ethoxy, propoxy and butoxy), halo-$C_{1-6}$ alkoxy (eg. trifluoromethoxy), halo-$C_{1-6}$-alkyl (eg. trifluoromethyl), nitro, phenyl and phenoxy. The phenyl ring may thus be unsubstituted or substituted with ring substituents as defined above and such substituents may be at the 2-, 3- or 4-positions of the phenyl ring and the 4-position is preferred.

Haloalkyl groups represented by A, B, X or Y may be chloromethyl, chloroethyl, chloropropyl and chlorobutyl; and their fluoro equivalents.

The

group represented by A, B, X or Y wherein $R^9$, $R^{10}$ and $R^{11}$, which may be the same or different, represent an alkyl group containing up to 4 carbon atoms, an alkenyl or alkynyl group each containing from 2 to 4 carbon atoms, a cycloalkyl group containing from 3 to 6 carbon atoms, a cycloalkylalkyl group containing from 4 to 7 carbon atoms or a phenyl group.

The acid addition salts of the compounds of the invention may be salts with inorganic or organic acids eg. hydrochloric, nitric, sulphuric, acetic, 4-toluenesulphonic or oxalic acid.

The invention is illustrated by Tables I and II below in which specific compounds are exemplified corresponding to the general formula at the head of the table.

TABLE I $$\underset{B}{\overset{A}{\diagdown}}C=\underset{Z}{\overset{X}{\diagup}}C\underset{R^3}{\overset{R^1}{-}}C\underset{R^4}{\overset{R^2}{-}}C\underset{R^6}{\overset{R^5}{-}}N\underset{R^8}{\overset{R^7}{\diagdown}}$$

| COMPOUND NO. | A | B | X | Z | $R^1$ | $R^2$ | $R^3$ | $R^4$ | $R^5$ | $R^6$ | $-N\begin{array}{c}R^7\\R^8\end{array}$ | m.p./b.p. | COMMENTS* |
|---|---|---|---|---|---|---|---|---|---|---|---|---|---|
| 1 | H | t-Bu | H | O | H | H | H | H | H | H | morpholine 3,5-diCH₃ (cis) | Oil | trans Het/CH₂ cis CH₃/CH₃ |
| 2 | H | t-Bu | H | O | H | H | H | H | H | H | morpholine 3,5-diCH₃ (trans) | | trans Het/CH₂ trans CH₃/CH₃ |
| 3 | H | t-Bu | H | O | H | H | H | H | H | H | piperidine | Oil | trans Het/CH₂ |
| 4 | H | t-Bu | H | S | H | H | H | H | H | H | morpholine 3,5-diCH₃ | Oil | trans Het/CH₂ cis CH₃/CH₃ |
| 5 | H | t-Bu | H | S | H | H | H | H | H | H | morpholine 3,5-diCH₃ | Oil | cis Het/CH₂ cis CH₃/CH₃ |
| 6 | H | t-Bu | H | S | H | H | H | H | H | H | piperidine | Oil | trans Het/CH₂ |
| 7 | H | t-Bu | H | S | H | H | H | H | H | H | piperidine | Oil | cis Het/CH₂ |
| 8 | H | n-Bu | H | S | H | H | H | H | H | H | morpholine 3,5-diCH₃ | Oil | trans Het/CH₂ cis CH₃/CH₃ |
| 9 | H | n-Bu | H | S | H | H | H | H | H | H | morpholine 3,5-diCH₃ | Oil | cis Het/CH₂ cis CH₃/CH₃ |
| 10 | H | n-Bu | H | S | H | H | H | H | H | H | piperidine | Oil | trans Het/CH₂ |
| 11 | H | n-Bu | H | S | H | H | H | H | H | H | piperidine | Oil | cis Het/CH₂ |

TABLE I-continued

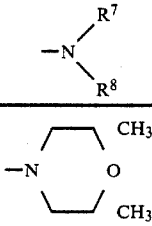

| COMPOUND NO. | A | B | X | Z | R¹ | R² | R³ | R⁴ | R⁵ | R⁶ | −N(R⁷)(R⁸) | m.p./b.p. | COMMENTS* |
|---|---|---|---|---|---|---|---|---|---|---|---|---|---|
| 12 | H | n-Bu | H | O | H | H | H | H | H | H | 2,6-dimethylmorpholino | Oil | cis Het/CH₂ <br> cis CH₃/CH₃ |
| 13 | H | n-Bu | H | O | H | H | H | H | H | H | piperidino | Oil | cis Het/CH₂ |
| 14 | H | H | H | S | H | H | H | H | H | H | piperidino | | trans Het/CH₂ |
| 15 | H | H | H | S | H | H | H | H | H | H | piperidino | | cis Het/CH₂ |
| 16 | H | H | H | S | H | H | H | H | H | H | 2,6-dimethylmorpholino | Oil | trans Het/CH₂ <br> cis CH₃/CH₃ |
| 17 | H | H | H | S | H | H | H | H | H | H | 2,6-dimethylmorpholino | Oil | cis Het/CH₂ <br> cis CH₃/CH₃ |
| 18 | H | Br | H | S | H | H | H | H | H | H | piperidino | | trans Het/CH₂ |
| 19 | H | Br | H | S | H | H | H | H | H | H | piperidino | | cis Het/CH₂ |
| 20 | H | Br | H | S | H | H | H | H | H | H | 2,6-dimethylmorpholino | | trans Het/CH₂ <br> cis CH₃/CH₃ |
| 21 | H | Br | H | S | H | H | H | H | H | H | 2,6-dimethylmorpholino | | cis Het/CH₂ <br> cis CH₃/CH₃ |
| 22 | H | (CH₃)₃Si | H | S | H | H | H | H | H | H | piperidino | | trans Het/CH₂ |

TABLE I-continued

| COMPOUND NO. | A | B | X | Z | R¹ | R² | R³ | R⁴ | R⁵ | R⁶ | $-N\begin{matrix}R^7\\R^8\end{matrix}$ | m.p./b.p. | COMMENTS* |
|---|---|---|---|---|---|---|---|---|---|---|---|---|---|
| 23 | H | (CH₃)₃Si | H | S | H | H | H | H | H | H |  | | cis Het/CH₂ |
| 24 | H | (CH₃)₃Si | H | S | H | H | H | H | H | H |  | | trans Het/CH₂ cis CH₃/CH₃ |
| 25 | H | (CH₃)₃Si | H | S | H | H | H | H | H | H |  | | cis Het/CH₂ cis CH₃/CH₃ |
| 26 | H | (CH₃)₃Si | H | O | H | H | H | H | H | H |  | | trans Het/CH₂ |
| 27 | H | (CH₃)₃Si | H | O | H | H | H | H | H | H |  | | cis Het/CH₂ |
| 28 | H | (CH₃)₃Si | H | O | H | H | H | H | H | H |  | | trans Het/CH₂ cis CH₃/CH₃ |
| 29 | H | (CH₃)₃Si | H | O | H | H | H | H | H | H |  | | cis Het/CH₂ cis CH₃/CH₃ |
| 30 | H | t-Bu | H | S | H | H | CH₃ | H | H | H |  | | trans Het/CH₂ |
| 31 | H | t-Bu | H | S | H | H | CH₃ | H | H | H |  | | cis Het/CH₂ |
| 32 | H | t-Bu | H | S | H | H | CH₃ | H | H | H |  | | trans Het/CH₂ cis CH₃/CH₃ |
| 33 | H | t-Bu | H | S | H | H | CH₃ | H | H | H |  | | cis Het/CH₂ cis CH₃/CH₃ |

TABLE I-continued

[Structure diagram showing compound with substituents A, B, X, Z, R¹-R⁸ and C-C-C-N backbone]

| COMPOUND NO. | A | B | X | Z | R¹ | R² | R³ | R⁴ | R⁵ | R⁶ | $-N{\stackrel{R^7}{R^8}}$ | m.p./b.p. | COMMENTS* |
|---|---|---|---|---|---|---|---|---|---|---|---|---|---|
| 34 | H | t-Bu | H | S | CH₃ | H | H | H | H | H | piperidinyl | | trans Het/CH₂, trans Het/CH₃ |
| 35 | H | t-Bu | H | S | CH₃ | H | H | H | H | H | piperidinyl | | cis Het/CH₂, trans Het/CH₃ |
| 36 | H | t-Bu | H | S | CH₃ | H | H | H | H | H | 3,5-dimethylmorpholinyl | | trans Het/CH₂, trans Het/CH₃, cis CH₃/CH₃ |
| 37 | H | t-Bu | H | S | CH₃ | H | H | H | H | H | 3,5-dimethylmorpholinyl | | cis Het/CH₂, trans Het/CH₃, cis CH₃/CH₃ |

TABLE II

[Structure diagram showing compound with substituents A, B, Y, Z, R¹-R⁸ and C-C-C-N backbone]

| COMPOUND NO. | A | B | Y | Z | R¹ | R² | R³ | R⁴ | R⁵ | R⁶ | $-N{\stackrel{R^7}{R^8}}$ | m.p./b.p. | COMMENTS* |
|---|---|---|---|---|---|---|---|---|---|---|---|---|---|
| 38 | H | H | H | S | H | H | H | H | H | H | piperidinyl | | trans Het/CH₂ |
| 39 | H | H | H | S | H | H | H | H | H | H | piperidinyl | | cis Het/CH₂ |
| 40 | H | H | H | S | H | H | H | H | H | H | 3,5-dimethylmorpholinyl | | trans Het/CH₂, cis CH₃/CH₃ |
| 41 | H | H | H | S | H | H | H | H | H | H | 3,5-dimethylmorpholinyl | | cis Het/CH₂, cis CH₃/CH₃ |

TABLE II-continued

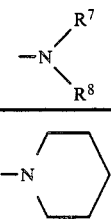

| COMPOUND NO. | A | B | Y | Z | R¹ | R² | R³ | R⁴ | R⁵ | R⁶ | $-N\genfrac{}{}{0pt}{}{R^7}{R^8}$ | m.p./b.p. | COMMENTS* |
|---|---|---|---|---|---|---|---|---|---|---|---|---|---|
| 42 | H | t-Bu | H | S | H | H | H | H | H | H | —N(piperidine) | | trans Het/CH₂ |
| 43 | H | t-Bu | H | S | H | H | H | H | H | H | —N(piperidine) | | cis Het/CH₂ |
| 44 | H | t-Bu | H | S | H | H | H | H | H | H | —N(2,6-dimethylmorpholine) | | trans Het/CH₂ cis CH₃/CH₃ |
| 45 | H | t-Bu | H | S | H | H | H | H | H | H | —N(2,6-dimethylmorpholine) | | cis Het/CH₂ cis CH₃/CH₃ |
| 46 | H | (CH₃)₃Si | H | S | H | H | H | H | H | H | —N(piperidine) | | trans Het/CH₂ |
| 47 | H | (CH₃)₃Si | H | S | H | H | H | H | H | H | —N(piperidine) | | cis Het/CH₂ |
| 48 | H | (CH₃)₃Si | H | S | H | H | H | H | H | H | —N(2,6-dimethylmorpholine) | | trans Het/CH₂ cis CH₃/CH₃ |
| 49 | H | (CH₃)₃Si | H | S | H | H | H | H | H | H | —N(2,6-dimethylmorpholine) | | cis Het/CH₂ cis CH₃/CH₃ |
| 50 | H | H | H | O | H | H | H | H | H | H | —N(piperidine) | | trans Het/CH₂ |
| 51 | H | H | H | O | H | H | H | H | H | H | —N(2,6-dimethylmorpholine) | | trans Het/CH₂ cis CH₃/CH₃ |

*'Het' signifies the unsaturated heterocyclic ring.

Compounds of general formula (III) can be prepared by treatment of a compound of general formula (IV):

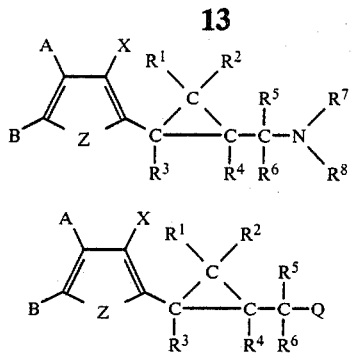   (III)

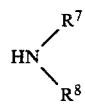   (IV)

wherein R$^1$ to R$^6$, A, B, X and Z are as defined above and Q is a leaving group such as chlorine, bromine, mesylate or tosylate, with an amine of general formula (V):

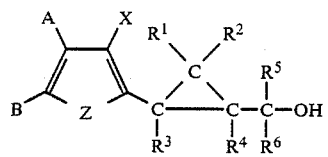   (V)

wherein R$^7$ and R$^8$ are as defined above, in the presence of a convenient solvent such as ethanol or tetrahydrofuran, or, preferably, in the absence of a solvent at a temperature of 20°–100° C. The compounds (IV) can be prepared by treating an alcohol of general formula (VI):

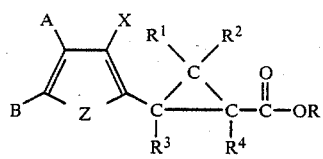   (VI)

wherein R$^1$ to R$^6$, A, B, X and Z are as defined above, with the usual halogenating agents (for example phosphorus trichloride, phosphorus pentachloride, or phosphorus oxychloride when Q=chlorine and phosphorus tribromide, phosphorus pentabromide, or phosphorus oxybromide when Q=bromine), or mesyl chloride in pyridine (or triethylamine) when Q=mesylate, or tosyl chloride in pyridine (or triethylamine) when Q=tosylate.

The alcohols (VI), wherein R$^5$=R$^6$=hydrogen, can be prepared by treating an ester of general formula (VII):

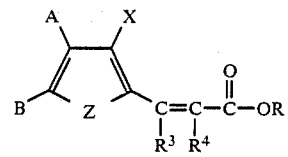   (VII)

wherein R$^1$, R$^2$, R$^3$, R$^4$, A, B, X and Z are as defined above and R is alkyl, with a reducing agent (usually lithium aluminium hydride) in a convenient solvent such as diethyl ether or tetrahydrofuran.

The alcohols (VI), wherein R$^5$=R$^6$=alkyl, can be prepared by treating the above ester (VII) with an excess of alkyl magnesium halide or an excess of alkyl lithium in a convenient solvent such as diethyl ether or tetrahydrofuran.

The cyclopropane esters (VII) can be prepared by reacting the unsaturated esters of general formula (VIII):

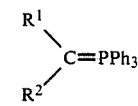   (VIII)

wherein R, R$^3$, R$^4$, A, B, X and Z are as defined above, with a phosphorane of general formula (IX):

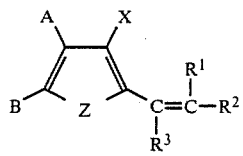   (IX)

wherein R$^1$ and R$^2$ are as defined above except that R$^1$ and R$^2$ cannot be halogen atoms, in a convenient solvent such as tetrahydrofuran.

In an alternative process the esters of general formula (VII) wherein R$^4$=hydrogen can be prepared by adding ethyl diazoacetate to the olefin of general formula (X):

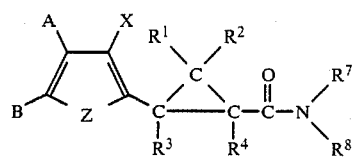   (X)

wherein R$^1$, R$^2$, R$^3$, A, B, X and Z are as defined above, in a convenient solvent such as chloroform or dichloromethane using an appropriate catalyst such as anhydrous copper (II) sulphate.

The compounds of general formula (III) wherein R$^5$=R$^6$=hydrogen can also be prepared by treating an amide of general formula (XI):

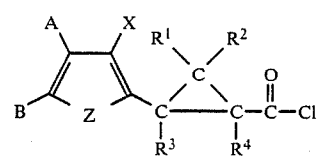   (XI)

wherein R$^1$ to R$^4$, R$^7$ and R$^8$, A, B, X and Z are as defined above, with a reducing agent (usually lithium aluminium hydride) in a convenient solvent such as diethyl ether or tetrahydrofuran.

The amides of general formula (XI) can be prepared by reacting an acid chloride of general formula (XII):

(XII)

wherein R$^1$ to R$^4$, A, B, X and Z are as defined above, with an amine of general formula (V):

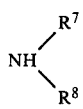
(V)

in a convenient solvent such as diethyl ether or tetrahydrofuran.

The acid chlorides of general formula (XII) can be prepared by reacting an acid of general formula (XIII):

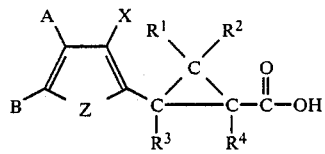
(XIII)

wherein $R^1$ to $R^4$, A, B, X and Z are as defined above, with the usual chlorinating agents such as thionyl chloride or oxalyl chloride in a convenient solvent such as hexane or dichloromethane.

The acids of general formula (XIII) can be prepared by hydrolysing the esters (VII) in the normal manner using either sodium or potassium hydroxide in methanol/water solution at 20°-60° C.

It is normal for compounds of general formula (VI) when $R^1 = R^2 =$ halogen to be prepared from the substituted allyl alcohol (XIV):

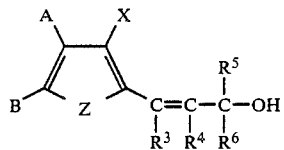
(XIV)

wherein $R^3$ to $R^6$, A, B, X and Z are as defined above by by the addition of a dihalocarbene in a convenient solvent such as chloroform or dichloromethane.

In an alternative process esters of general formula (VII) can be prepared by treating compounds of general formula (XV):

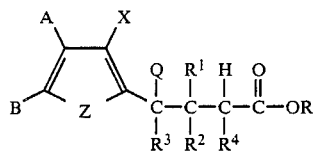
(XV)

wherein $R^1$ to $R^4$, R, A, B, X, Z, and Q are as defined above, with a base such as sodium alkoxide or sodium hydride in a convenient solvent at a temperature of 20°-100° C. The compounds of general formula (XV) can be prepared by methods set out in the literature.

Also the alcohols of the general formula (VI) can be prepared by carrying out a Simmons-Smith reaction on the compounds of general formula (XIV).

Compounds of general formula (XVI):

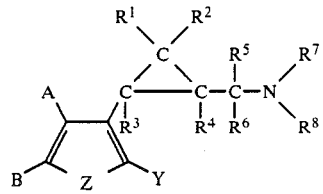
(XVI)

wherein $R^1$ to $R^8$, A, B, Y and Z are as defined above can be prepared by the methods described previously for the preparation of compounds (III).

The salts of compounds (III) and (XVI) may be prepared from the latter by known methods.

The salts of compounds of the general formula (I) can be prepared from the latter by known methods.

The compounds, and their acid addition salts are active fungicides, particularly against the diseases *Puccinia recondita, Puccinia striiformis* and other rusts on wheat, *Puccinia hordei, Puccina striiformis* and other rusts on barley, and rusts on other hosts e.g. coffee, apples, apples, vegetables and ornamental plants, *Erysiphe graminis* (powdery mildew) on barley and wheat and other powdery mildews on various hosts such as *Sphaerotheca fuliginea* on cucurbits (e.g. cucumber), *Podosphaera leucotricha* on apples and *Uncinula necator* on vines, *Cercospora arachidicola* on peanuts and other Cercospora species on for example sugar beet, bananas and soya beans *Venturia inaequalis* (scab) on apples.

Some of the compounds have also shown a broad range of activities against fungi in vitro. They have activity against various post-harvest diseases on fruit (e.g. *Penicillium diagatatum* and *italicum*, and *Trichoderma viride* on oranges, *Gloeosporium musarum* on bananas and *Botrytis cinerea* on grape).

The compounds can move acropetally in the plant tissue. Moreover, the compounds can be volatile enough to be active in the vapour phase against fungi on the plant.

They may also be useful as industrial (as opposed to agricultural) fungicides, e.g. in the prevention of fungal attack on wood, hides, leather and especially paint films.

The compounds are also useful for the treatment of human fungal infections, such as, for example, candidiasis and dermatophyte infections.

The compounds may be used as such for fungicidal purposes but are more conveniently formulated into compositions for such usage. The invention thus provides a fungicidal composition comprising a compound of general formula (I) as hereinbefore defined, or an acid addition thereof; and, optionally, a carrier or diluent.

The invention also provides a method of combating fungi, which comprises applying to a plant, a seed of a plant, or to the locus of the plant or seed, a compound, or an acid addition salt thereof, as hereinbefore defined.

The compounds and their acid addition salts can be applied in a number of ways, for example they can be applied, formulated or unformulated, directly to the foliage of a plant, or they can be applied also to bushes and trees, to seeds or to other medium in which plants, bushes or trees are growing or are to be planted, or they can be sprayed on, dusted on or applied as a cream or paste formulation, or they can be applied as a vapour; or as slow release granules. Application can be to any part of the plant, bush or tree, for example to the foliage, stems, branches or roots, or to soil surrounding the roots, or to the seed before it is planted; or to the soil generally, to paddy water or to hydroponic culture systems. The invention compounds may also be injected into plants or trees and they may also be sprayed onto vegetation using electrodynamic spraying techniques.

The term "plant" as used herein includes seedlings, bushes and trees. Furthermore, the fungicidal method of the invention includes preventative, protectant, prophylactic and eradicant treatment.

The compounds are preferably used for agricultural and horticultural purposes in the form of a composition. The type of composition used in any instance will depend upon the particular purpose envisaged.

The compounds may be used as such for fungicidal purposes but are more conveniently formulated into compositions for such usage. The invention thus provides a fungicidal composition comprising a compound of general formula (I) as hereinfore defined, or an acid addition thereof; and, optionally, a carrier or diluent.

The invention also provides a method of combating fungi, which comprises applying to a plant, to seed of a plant, or to the locus of the plant or seed, a compound, or an acid addition salt thereof, as hereinbefore defined.

The compounds and their acid addition salts can be applied in a number of ways, for example they can be applied, formulated or unformulated, directly to the foliage of a plant, or they can be applied also to bushes and trees, to seeds or to other medium in which plants, bushes or trees are growing or are to be planted, or they can be sprayed on, dusted on or applied as a cream or paste formulation, or they can be applied as a vapour; or as slow release granules. Application can be to any part of the plant, bush or tree, for example to the foliage, stems, branches or roots, or to soil surrounding the roots, or to the seed before it is planted; or to the soil generally, to paddy water or to hydroponic culture systems. The invention compounds may also be injected into plants or trees and they may also be sprayed onto vegetation using electrodynamic spraying techniques.

The term "plant" as used herein includes seedlings, bushes and trees. Furthermore, the fungicidal method of the invention includes preventative, protectant, prophylactic and eradicant treatment.

The compounds are preferably used for agricultural and horticultural purposes in the form of a composition. The type of composition used in any instance will depend upon the particular purpose envisaged.

The compositions may be in the form of dusting powders or granules comprising the active ingredient and a solid diluent or carrier, for example fillers such as kaolin, bentonite, kieselguhr, dolomite, calcium carbonate, talc, powdered magnesia, Fuller's earth, gypsum, Hewitt's earth, diatomaceous earth and China clay. Such granules can be preformed granules suitable for application to the soil without further treatment. These granules can be made either by impregnating pellets of filler with the active ingredient or by pelleting a mixture of the active ingredient and powdered filler. Compositions for dressing seed, for example, may comprise an agent (for example a mineral oil) for assisting the adhesion of the composition to the seed; alternatively the active ingredient can be formulated for seed dressing purposes using an organic solvent (for example N-methylpyrrolidone or dimethylformamide).

The compositions may also be in the form of dispersible powders, granules or grains comprising a wetting agent to facilitate the dispersion in liquids of the powder or grains which may contain also fillers and suspending agents.

The aqueous dispersions or emulsions may be prepared by dissolving the active ingredient(s) in an organic solvent optionally containing wetting, dispersing or emulsifying agent(s) and then adding the mixture of water which may also contain wetting, dispersing or emulsifying agent(s). Suitable organic solvents are ethylene dichloride, isopropyl alcohol, propylene glycol, diacetone alcohol, toluene, kerosene, methylnaphthalene, the xylenes, trichloroethylene, furfuryl alcohol, tetrahydrofurfuryl alcohol, and glycol ethers (eg. 2-ethoxyethanol and 2-butoxyethanol).

The compositions to be used as sprays may also be in the form of aerosols wherein the formulation is held in a container under pressure in the presence of a propellant, eg. fluorotrichloromethane or dichlorodifluoromethane.

The compounds can be mixed in the dry state with a pyrotechnic mixture to form a composition suitable for generating in enclosed spaces a smoke containing the compounds.

Alternatively, the compounds may be used in a microencapsulated form. They may also be formulated in biodegradable polymeric formulations to obtain a slow, controlled release of the active substance.

By including suitable additives, for example additives for improving the distribution, adhesive power and resistance to rain on treated surfaces, the different compositions can be better adapted for various utilities.

The compounds can be used as mixtures with fertilisers (eg. nitrogen-, potassium- or phosphorus-containing fertilisers). Compositions comprising only granules of fertiliser incorporating, for example coated with, the compound are preferred. Such granules suitably contain up to 25% by weight of the compound. The invention therefore also provides a fertiliser composition comprising the compound of general formula (I) or a salt thereof.

The compositions may also be in the form of liquid preparations for use as dips or sprays which are generally aqueous dispersions or emulsions containing the active ingredient in the presence of one or more surfactants eg. wetting agent(s), dispersing agent(s), emulsifying agent(s) or suspending agent(s); or which are spray formulations of the kind suitable for use in electrodynamic spraying techniques. The foregoing agents can be cationic, anionic or non-ionic agents. Suitable cationic agents are quaternary ammonium compounds, for example cetyltrimethylammonium bromide.

Suitable anionic agents are soaps, salts of aliphatic monoesters of sulphuric acid (for example sodium lauryl sulphate), and salts of sulphonated aromatic compounds (for example sodium dodecylbenzenesulphate, sodium, calcium or ammonium lignosulphonate, butylnaphthalene sulphonate, and a mixture of sodium diisopropyl- and triisopropyl-naphthalene sulphonates).

Suitable non-ionic agents are the condensation products of ethylene oxide with fatty alcohols such as oleyl or cetyl alcohol, or with alkyl phenols such as octyl- or nonyl-phenol and octylcresol. Other non-ionic agents are the partial esters derived from long chain fatty acids and hexitol anhydrides, the condensation products of the said partial esters with ethylene oxide, and the lecithins. Suitable suspending agents are hydrophilic colloids (for example polyvinylpyrrolidone and sodium carboxymethylcellulose), and the vegetable gums (for example gum acacia and gum tragacanth).

The compositions for use as aqueous dispersions or emulsions are generally supplied in the form of a concentrate containing a high proportion of the active ingredient(s), and the concentrate is to be diluted with water before use. These concentrates often should be able to withstand storage for prolonged periods and after such storage be capable of dilution with water in order to form aqueous preparations which remain homogeneous for a sufficient time to enable them to be applied by conventional and electrodynamic spray equipment. The concentrates may conveniently contain up to 95%, suitably 10–85%, for example 25–60%, by weight of the active ingredient(s). These concentrates suitably contain organic acids (eg. alkaryl or aryl sulphonic acids such as xylenesulphonic acid or dodecyl benzenesulphonic acid) since the presence of such acids can increase the solubility of the active ingredient(s) in the polar solvents often used in the concentrates. The concentrates suitably contain also a high proportion of surfactants so that sufficiently stable emulsions in water can be obtained. After dilution to form aqueous preparations, such preparations may contain varying amounts of the active ingredient(s) depending upon the intended purpose, but an aqueous preparation containing 0.0005% or 0.01% to 10% by weight of active ingredient(s) may be used.

The compositions of this invention can comprise also other compound(s) having biological activity, eg. compounds having similar or complementary fungicidal activity or compounds having plant growth regulating, herbicidal or insecticidal activity.

The other fungicidal compound can be, for example, one which is capable of combating ear diseases of cereals (eg. wheat) such as Septoria, Gibberella and Helminthosporium spp., seed and soil-borne diseases and downy and powdery mildews on grapes and powdery mildew and scab on apple etc. These mixtures of fungicides can have a broader spectrum of activity than the compound of general formula (I) alone; further the other fungicide can have a synergistic effect on the fungicidal activity of the compound of general formula (I). Examples of the other fungicidal compound are carbendazim, benomyl, thiophanatemethyl, thiabendazole, fuberidazole, etridazole, dichlofluanid, cymoxanil, oxadixyl, ofurace, metalaxyl, furalaxyl, benalaxyl, fosetyl aluminium, fenarimol, iprodione, procymidione, vinclozolin, penconazole, myclobutanil, R0151297, S3308, pyrazophos, ethirimol, ditalimfos, tridemorph, triforine, nuarimol, triazbutyl, guazatine, triacetate salt of 1,1'-iminodi(octamethylene)diguanidine, propiconazole, prochloraz, flutriafol, hexaconazole ie. the chemical 1-(1,2,4-triazol-1-yl)-2-(2,4-dichlorophenyl)hexan-2-ol, DPX H6573(1-((bis-4-fluorophenyl)methylsilyl)methyl)1H-1,2,4-triazole, triadimefon, triadimenol, diclobutrazol, fenpropimorph, pyrifenox, (2RS, 3RS)-2-(4-chlorophenyl)-3-cyclopropyl-1-(1H-1,2,4-triazol-1-yl)butan-2-ol, (RS)-1-(4-chlorophenyl)-4,4-dimethyl-3-(1H-1,2,4-triazol-1-ylmethyl)-pentan-3-ol, 4-chloro-N-(cyano(ethoxy)methyl)benzamide, fenpropidin, chlorozolinate, diniconazol, imazalil, fenfuram, carboxin, oxycarboxin, methfuroxam, dodemorph, BAS 454, blasticidin S, kasugamycin, edifenphos, kitazin P, cycloheximide, phthalide, probenazole, isoprothiolane, tricyclazole, pyroquilon, chlorbenzthiazone, neoasozin, polyoxin D, validamycin A, mepronil, flutolanil, pencycuron, diclomezine, phenazin oxide, nickel dimethyldithiocarbamate, techlofthalam, bitertanol, bupirimate, etaconazole, streptomycin, cypofuram, biloxazol, quinomethionate, dimethirimol, 1-(2-cyano-2-methoxyimino-acetyl)-3-ethyl urea, fenapanil, tolclofos-methyl, pyroxyfur, polyram, maneb, mancozeb, captafol, chlorothalonil, anilazine, thiram, captan, folpet zineb, propineb, sulphur, dinocap, binapacryl, nitrothal-isopropyl, dodine, dithianon, fentin hydroxide, fentin acetate, tecnazene, quintozene, dichloran, copper containing compounds such as copper oxychloride, copper sulphate and Bordeaux mixture, and organomercury compounds.

The compounds of general formula (I) can be mixed with soil, peat or other rooting media for the protection of plants against seed-borne, soil-borne or foliar fungal diseases.

Suitable insecticides which may be incorporated in the composition of the invention include pirimicarb, dimethoate, demeton-s-methyl, formothion, carbaryl, isoprocarb, XMC, BPMC, carbofuran, carbosulfan, diazinon, fenthion, fenitrothion, phenthoate, chlorpyrifos, isoxathion, propaphos, monocrotophos, buprofezin, ethroproxyfen and cycloprothrin.

Plant growth regulating compounds for use in the invention compositions are compounds which control weeds or seedhead formation, or selectively control the growth of less desirable plants (e.g. grasses).

Examples of suitable plant growth regulating compounds for use with the invention compositions are the gibberellins (e.g. $GA_3$, $GA_4$ or $GA_7$), the auxins (e.g. indoleacetic acid, indolebutyric acid, naphthoxyacetic acid or naphthylacetic acid), the cytokinins (e.g. kinetin, diphenylurea, benzimidazole, benzyladenine or benzylaminopurine), phenoxyacetic acids (e.g. 2,4-D or MCPA), substituted benzoic acids (e.g. triiodobenzoic acid), morphactins (e.g. chlorfluoroecol), maleic hydrazide, glyphosate, glyphosine, long chain fatty alcohols and acids, dikegulac, paclobutrazol, flurprimidol, fluoridamid, mefluidide, substituted quaternary ammonium and phosphonium compounds (e.g. chloromequat chlorphonium or mepiquatchloride), ethephon, carbetamide, methyl-3,6-dichloroanisate, daminozide, asulam, abscisic acid, isopyrimil, 1-(4-chlorophenyl)-4,6-dimethyl-2-oxo-1,2-dihydropyridine-3-carboxylic acid, hydroxybenzonitriles (e.g. bromoxynil), difenzoquat, benzoylprop-ethyl 3,6-dichloropicolinic acid, fenpentezol, inabenfide, triapenthenol and tecnazene.

The following Examples illustrate the invention; the temperatures are given in degrees Centigrade (°C).

EXAMPLE 1

This Example illustrates the preparation of 4-[2-(5-n-butylthiophen-2-yl)-trans-cyclopropylmethyl]-2,6-cis-dimethylmorpholine (Compound No. 8 in Table I). Phosphorus oxychloride (12.02 g, 0.078 mol) was added dropwise to N-methylformanilide (10.62 g, 0.079 mol) and a yellow solid was produced. This was cooled to 0° C. for ½ hour, then 2-n-butylthiophene (10 g, 0.071 mol) was added dropwise and the mixture stirred at room temperature for 3 hours. The mixture was poured into ice/water, neutralised with sodium carbonate and extracted into diethyl ether. The ethereal extracts were washed with water, dried over anhydrous sodium sulphate and the solvent removed to give a brown oil. Purification by column chromatography (silica eluted with petroleum ether/ethyl acetate 9:1) gave 5-n-butyl-2-thiophenecarboxaldehyde (11.8 g, 99%). Sodium hydride (6.63 g-50% suspension in oil, 0.138 mol) was washed with petroleum ether, suspended in dry DMSO (100 ml) and heated with stirring at 60°–70° C. for 2 hours. The reaction mixture was then cooled to 15° C. and methyltriphenylphosphonium bromide (48.72 g, 0.136 mol) was added portionwise with rapid stirring over a ½ hour period. The reaction mixture was stirred at room temperature for a further 1 hour after the addition and 5-n-butyl-2-thiophenecarboxaldehyde (23 g, 0.137 mol) was added dropwise over a period of 1 hour. The resultant reaction mixture was stirred at room temperature for 12 hours, poured into water (300 ml) and extracted with ether (4×150 ml). The ethereal extracts were washed with water (4×100 ml) and dried over anhydrous sodium sulphate. Removal of the solvent gave a yellow oil which was purified by column chromatography (silica eluted with petroleum ether/ethyl acetate 9:1) to give (5-n-butylthiophen-2-yl)-ethylene (18.5 g, 82%). Ethyl diazoacetate (13.0 g, 0.11 mol) in dry dichloromethane (150 ml) was added dropwise to a solution of (5-n-butylthiophen-2-yl)-ethylene (18.3 g, 0.11 mol) and anhydrous copper (II) sulphate (0.3 g) in dry dichloromethane (50 ml) at 90° C. by means of a syringe pump over a period of 5 hours. The dichloromethane was distilled over during the addition. After complete addition the remaining dichloromethane was removed in vacuo and the resulting brown oil purified by column chromatography (silica eluted with petroleum ether/ethyl acetate 1:1) to give ethyl 2-(5-n-butylthiophen-2-yl)-cyclopropanecarboxylate (18 g, 71%).

Ethyl 2-(5-n-butylthiophen-2-yl)-cyclopropanecarboxylate (12.6 g, 0.05 mol) was dissolved in methanol (70 ml) and a solution of potassium hydroxide (6.5 g, 0.12 mol) in water (70 ml) added dropwise at room temperature. The solution was refluxed for 3 hours, cooled to room temperature and carefully neutralised with 2M HCl. Saturated sodium chloride was added, the aqueous solution extracted with ethyl acetate (4×75 ml) and dried over anhydrous sodium sulphate. Removal of the solvent gave 2-(5-n-butylthiophen-2-yl)-cyclopropanecarboxylic acid (10.0 g, 89%).

A mixture of 2-(5-n-butylthiophen-2-yl)-cyclopropanecarboxylic acid (9.0 g, 0.04 mol) and oxalyl chloride (6.35 g, 0.05 mol) in hexane (70 ml) was stirred at room temperature for 2 hours and then warmed at 60° C. for 3 hours. The hexane and excess oxalyl chloride were removed in vacuo to give 2-(5-n-butylthiophen-2-yl)-cyclopropanecarbonyl chloride (9.7 g, 100%) as a pale yellow liquid which was used in the next stage without further purification.

2,6-Dimethylmorpholine (5.0 g, 0.043 mol) was added dropwise to a solution of 2-(5-n-butylthiophen-2-yl)-cyclopropanecarbonyl chloride (4.85 g, 0.02 mol) in sodium dried ether (40 ml) at 10° C. and after complete addition the solution was stirred at 20° C. for 3 hours. The reaction mixture was poured into water and extracted with diethyl ether (2×100 ml). The ethereal extracts were washed with water, dried over anhydrous sodium sulphate, and the solvent removed to give 2-(5-n-butylthiophen-2-yl)-cyclopropanecarbonyl-2,6-dimethylmorpholine (5.8 g, 90% as a yellow oil. A solution of 2-(5-n-butylthiophen-2-yl)-chclopropanecarbonyl-2,6-dimethylmorpholine (5.8 g, 0.018 mol) in sodium dried ether (30 ml) was added dropwise to a suspension of lithium aluminium hydride (0.8 g, 0.02 mol) in sodium dried ether (20 ml) and the reaction mixture stirred at room temperature for 3 hours. The reaction mixture was poured carefully into water and extracted with diethyl ether. The ethereal extracts were washed with water, dried over anhydrous sodium sulphate, and the solvent removed to give a colourless oil. This oil was purified by column chromatography (silica eluted with ethyl acetate/petroleum ether 2:3) to give the title compound (1.3 g, 24%).

EXAMPLE 2

This Example illustrates the preparation of 4-[2-(5-t-butylthiophen-2-yl)-trans-cyclopropylmethyl]-2,6-cis-dimethylmorpholine (Compound No. 4 in Table I).

Phosphorus oxychloride (24.04 g, 0.157 mol) was added dropwise to N-methylformanilide (21.24 g, 0.157 mol) and a yellow solid was produced. This was cooled to 0° C. for ½ hour, then 2-t-butylthiophene (20 g, 0.143 mol) was added dropwise and the mixture stirred at room temperature for 3 hours. The mixture was poured into ice/water, neutralised with sodium bicarbonate and extracted into diethyl ether. The ethereal extracts were washed with water, dried over anhydrous sodium sulphate and the solvent removed to give a brown liquid. Purification by column chromatography (silica eluted with petroleum ether/ethyl acetate 9:1) gave 5-t-butyl-2-thiophenecarboxaldehyde (21.01 g, 87%) as a yellow liquid.

Sodium hydride (6.05 g-50% suspension in oil, 0.126 mol) was washed with petroleum ether, suspended in dry DMSO (90 ml) and heated with stirring at 60°–70° C. for 2 hours. The reaction mixture was then cooled to 15° C. and methyltriphenylphosphonium bromide (44.5 g, 0.125 mmol) was added portionwise with rapid stirring over a ½ hour period. The reaction mixture was stirred at room temperature for a further 1 hour after the addition and 5-t-butyl-2-thiophenecarboxaldehyde (21.01 g, 0.125 mol) was added dropwise over a period of 1 hour. The resultant reaction mixture was stirred at room temperature for 12 hours, poured into water (300 ml) and extracted with ether (4×150 ml). The ethereal extracts were washed with water (4×100 ml) and dried over anhydrous sodium sulphate. Removal of the solvent gave a yellow oil which was purified by column chromatography (silica eluted with hexane) to give (5-t-butylthiophen-2-yl)-ethylene (5.25 g, 25%). Ethyl diazoacetate (4.69 g, 0.041 mol) in dry dichloromethane (80 ml) was added dropwise to a solution of (5-t-butylthiophen-2-yl)-ethylene (5.1 g, 0.031 mol) and anhydrous copper (II) sulphate (0.3 g) in dry dichloromethane (20 ml) at 90° C. by means of a syringe pump over a period of 5 hours. The dichloromethane was distilled over during the addition. After complete addition the remaining dichloromethane was removed in vacuo and the resulting brown oil purified by column chromatography (silica eluted with petroleum ether/ethyl acetate 19:1) to give ethyl 2-(5-t-butylthiophen-2-yl)-cyclopropanecarboxylate (4.72 g, 60%).

Ethyl 2-(5-t-butylthiophen-2-yl)-cyclopropanecarboxylate (4.49 g, 0.018 mol) was dissolved in methanol (45 ml) and a solution of potassium hydroxide (1.99 g, 0.036 mol) in water (45 ml) added dropwise at room temperature. The solution was refluxed for 3 hours, cooled to room temperature and carefully neutralised with 2M HCl. Saturated sodium chloride was added, the aqueous solution extracted with ethyl acetate (4×50 ml) and dried over anhydrous sodium sulphate. Removal of the solvent gave 2-(5-t-butylthiophen-2-yl)-cyclopropanecarboxylic acid (3.79 g, 94%).

A mixture of 2-(5-t-butylthiophen-2-yl)-cyclopropanecarboxylic acid (3.38 g, 0.015 mol) and oxalyl chloride (2.65 g, 0.021 mol) in hexane (35 ml) was stirred at room temperature for 2 hours and then warmed at 60° C. for 3 hours. The hexane and excess oxalyl chloride were removed in vacuo to give 2-(5-t-butylthiophen-2-yl)-cyclopropanecarbonyl chloride (3.59 g, 99%) as a pale yellow liquid which was used in the next stage without further purification.

cis-2,6-Dimethylmorpholine (6.6 g, 0.057 mol) was added dropwise to a solution of 2-(5-t-butylthiophen-2-yl)-cyclopropanecarbonyl chloride (2.50 g, 0.01 mol) in sodium dried ether (20 ml) at 10° C. and after complete addition the solution was stirred at 20° C. for 3 hours. The reaction mixture was poured into water and extracted with diethyl ether (2×75 ml). The ethereal extracts were washed with water, dried over anhydrous sodium sulphate, and the solvent removed to give 2-(5-t-butylthiophen-2-yl)-cyclopropanecarbonyl-2,6-cis-dimethylmorpholine as a yellow oil. This oil was separated by column chromatography (silica eluted with petroleum ether/ethyl acetate 1:1) to give 2-(5-t-butylthiophen-2-yl)-trans-cyclopropanecarbonyl)-2,6-cis-dimethylmorpholine (1.70 g, 53%) and 2-(5-t-butylthiophen-2-yl)-cis-cyclopropanecarbonyl)-2,6-cis-dimethylmorpholine (0.94 g, 29%).

A solution of 2-(5-t-butylthiophen-2-yl)-trans-cyclopropanecarbonyl-2,6-cis-dimethylmorpholine (1.54 g, 0.0048 mol) in sodium dried ether (10 ml) was added dropwise to a suspension of lithium aluminium hydride (0.23 g, 0.006 mol) in sodium dried ether (10 ml) and the reaction mixture stirred at room temperature for 3 hours. The reaction mixture was poured carefully into water and extracted with diethyl ether. The ethereal extracts were washed with water, dried over anhydrous sodium sulphate and the solvent removed to give the title compound (1.39 g, 94%) as a colourless oil.

EXAMPLE 3

This Example illustrates the preparation of 4-[2-(5-t-butylfuran-2-yl)-trans-cyclopropylmethyl]-2,6-cis-dimethylmorpholine (Compound No. 1 in Table I).

Phosphorus oxychloride (26.75 g, 0.174 mol) was added dropwise to dimethylformamide (12.92 g, 0.177 mol). This mixture was cooled to 10° C. for ½ hour, then 2-t-butylfuran (18.45 g, 0.149 mol) was added dropwise and the mixture stirred at room temperature for 3 hours. The mixture was poured into ice/water, neutralised with sodium carbonate and extracted into diethyl ether. The ethereal extracts were washed with water, dried over anhydrous sodium sulphate and the solvent removed to give a brown oil. Purification by column chromatography (silica eluted with petroleum ether/ethyl acetate 9:1) gave 5-t-butyl-2-furancarboxaldehyde (22.46 g, 99%).

Sodium hydride (7.09 g-50% suspension in oil, 0.148 mol) was washed with petroleum ether, suspended in dry DMSO (100 ml) and heated with stirring at 60°–70° C. for 2 hours. The reaction mixture was then cooled to 15° C. and methyltriphenylphosphonium bromide (52.74 g, 0.136 mol) was added portionwise with rapid stirring over a ½ hour period. The reaction mixture was stirred at room temperature for a further 1 hour after the addition and 5-t-butyl-2-furancarboxaldehyde (22.46 g, 0.148 mol) was added dropwise over a period of 1 hour. The resultant reaction mixture was stirred at room temperature for 12 hours, poured into water (300 ml) and extracted with ether (4×150 ml). The ethereal extracts were washed with water (4×100 ml) and dried over anhydrous sodium sulphate. Removal of the solvent gave a yellow oil which was purified by column chromatography (silica eluted with petroleum ether) to give (5-t-butylfuran-2-yl)-ethylene (11.03 g, 50%). Ethyl diazoacetate (4.45 g, 0.039 mol) in dry dichloromethane (70 ml) was added dropwise to a solution of (5-t-butylfuran-2-yl)-ethylene (5.85 g, 0.039 mol) and anhydrous copper (II) sulphate (0.3 g) in dry dichloromethane (30 ml) at 90° C. by means of a syringe pump over a period of 5 hours. The dichloromethane was distilled over during the addition. After complete addition the remaining dichloromethane was removed in vacuo and the resulting brown oil purified by column chromatography (silica eluted with petroleum ether/ethyl acetate 9:1) to give ethyl 2-(5-t-butylfuran-2-yl)-cyclopropanecarboxylate (2.1 g, 23%).

Ethyl 2-(5-t-butylfuran-2-yl)-cyclopropanecarboxylate (5.0 g, 0.021 mol) was dissolved in methanol (50 ml) and a solution of potassium hydroxide (2.4 g, 0.043 mol) in water (50 ml) was added dropwise at room temperature. The solution was refluxed for 3 hours, cooled to room temperature and carefully neutralised with 2M HCl. Saturated sodium chloride was added, the aqueous solution extracted with ethyl acetate (4×50 ml) and dried over anhydrous sodium sulphate. Removal of the solvent gave 2-(5-t-butylfuran-2-yl)-cyclopropanecarboxylic acid (4.4 g, 100%).

A mixture of 2-(5-t-butylfuran-2-yl)-cyclopropanecarboxylic acid (3.6 g, 0.017 mol) and oxalyl chloride (4.4 g, 0.035 mol) in hexane (40 ml) was stirred at room temperature for 2 hours and then warmed at 60° C. for 3 hours. The hexane and excess oxalyl chloride were removed in vacuo to give 2-(5-t-butylfuran-2-yl)-cyclopropanecarbonyl chloride (3.9 g, 100%) as a pale yellow liquid which was used in the next stage without further purification.

cis-2,6-Dimethylmorpholine (8.9 g, 0.077 mol) was added dropwise to a solution of 2-(5-t-butylfuran-2-yl)-cyclopropanecarbonyl chloride (3.5 g, 0.0154 mol) in sodium dried ether (40 ml) at 10° C. and after complete addition the solution was stirred at 20° C. for 3 hours. The reaction mixture was poured into water and extracted with diethyl ether (2×100 ml). The ethereal extracts were washed with water, dried over anhydrous sodium sulphate, and the solvent removed to give 2-(5-t-butylfuran-2-yl)-cyclopropanecarbonyl-2,6-cis-dimethylmorpholine as a yellow oil. This oil was separated by column chromatography [silica eluted with petroleum ether ethyl acetate (1:1)] to give 2-(5-t-butylfuran-2-yl)-trans-cyclopropanecarbonyl-2,6-cis-dimethylmorpholine (1.43 g, 30%).

A solution of 2-(5-t-butylfuran-2-yl)-trans-cyclopropanecarbonyl-2,6-cis-dimethylmorpholine (2.19 g, 0.072 mol) in sodium dried ether (20 ml) was added dropwise to a suspension of lithium aluminium hydride (0.4 g, 0.011 mol) in sodium dried ether (20 ml) and the reaction mixture stirred at room temperature for 3 hours. The reaction mixture was poured carefully into water and extracted with diethyl ether. The ethereal extracts were washed with water, dried over anhydrous sodium sulphate, and the solvent removed to give the title compound (1.7 g, 81%) as a colourless oil.

EXAMPLE 4

An emulsifiable concentrate was made up by mixing the ingredients, and stirring the mixture until all the constituents were dissolved.

| | |
|---|---|
| Compound of Example 2 (Compound No. 4 of Table I) | 10% |
| Ethylene dichloride | 40% |
| Calcium dodecylbenzenesulphate | 5% |
| "Lubrol" L | 10% |
| "Aromasol" H | 35% |

EXAMPLE 5

A composition in the form of grains readily dispersible in a liquid, e.g. water, was prepared by grinding together the first three ingredients in the presence of added water and then mixing in the sodium acetate. The resultant mixture was dried and passed through a British Standard mesh sieve, size 44–100, to obtain the desired size of grains.

| | |
|---|---|
| Compound of Example 2 | 50% |
| "Dispersol" T | 25% |
| "Lubrol" APN5 | 1.5% |
| Sodium acetate | 23.5% |

EXAMPLE 6

The ingredients were all ground together to produce a powder formulation readily dispersible in liquids.

| | |
|---|---|
| Compound of Example 2 | 45% |
| "Dispersol" T | 5% |
| "Lissapol" NX | 0.5% |
| "Cellofas" B600 | 2% |
| Sodium acetate | 47.5% |

EXAMPLE 7

The active ingredient was dissolved in a solvent and the resultant liquid was sprayed on to the granules of China clay. The solvent was then allowed to evaporate to produce a granular composition.

| | |
|---|---|
| Compound of Example 2 | 5% |
| China clay granules | 95% |

EXAMPLE 8

A composition suitable for use as a seed dressing was prepared by mixing the three ingredients.

| | |
|---|---|
| Compound of Example 2 | 50% |
| Mineral oil | 2% |
| China clay | 48% |

EXAMPLE 9

A dusting powder was prepared by mixing the active ingredient with talc.

| | |
|---|---|
| Compound of Example 2 | 5% |
| Talc | 95% |

EXAMPLE 10

A Col formulation was prepared by ball-milling the constituents set out below and then forming an aqueous suspnesion of the ground mixture with water.

| | |
|---|---|
| Compound of Example 2 | 40% |
| "Dispersol" T | 10% |
| "Lubrol" APN5 | 1% |
| Water | |

EXAMPLE 11

A dispersible powder formulation was made by mixing together the ingredients set out below and then grinding the mixture until all were thoroughly mixed.

| | |
|---|---|
| Compound of Example 2 | 25% |
| "Aerosol" OT/B | 2% |
| "Dispersol" A.C. | 5% |
| China clay | 28% |
| Silica | 40% |

EXAMPLE 12

This Example illustrates the preparation of a dispersible pwoder formulation. The ingredients were mixed and the mixture then ground in a comminution mill.

| | |
|---|---|
| Compound of Example 2 | 25% |
| "Perminal" BX | 1% |
| "Dispersol" T | 5% |
| Polyvinylpyrrolidone | 10% |
| Silica | 25% |
| China clay | 34% |

EXAMPLE 13

The ingredients set out below were formulated into a dispersible powder by mixing then grinding the ingredients.

| | |
|---|---|
| Compound of Example 2 | 25% |
| "Aerosol" OT/B | 2% |
| "Dispersol" A | 5% |
| China clay | 68% |

In Examples 4 to 13 the proportions of the ingredients given are by weight.

The compounds set out in Tables I and II are numbered 1 to 3 and 5 to 51 can be similarly formulated as specifically described in Examples 4 to 13.

There now follows an explanation of the compositions or substances represented by the various Trade Marks mentioned above.

LUBROL L: a condensate of nonyl phenol (1 mol) with ethylene oxide (13 moles).

AROMASOL H: a solvent mixture of alkylbenzenes.

DISPERSOL T & AC: a mixture of sodium sulphate and a condensate of formaldehyde with sodium naphthalene sulphonate.

LUBROL APN5: a condensate of nonyl phenol (1 mole) with napthalene oxide (5.5 moles).

CELLOFAS B600: a sodium carboxymethyl cellulose thickener.

LISSAPOL NX: a condensate of nonyl phenol (1 mole) with ethylene oxide (8 moles).

AEROSOL OT/B: dioctyl sodium sulphosuccinate.
PERMINAL BX: a sodium alkyl naphthalene sulphonate.

EXAMPLE 14

The compounds were tested against a variety of foliar fungal diseases of plants. The technique employed was as follows.

The plants were grown in John Innes Potting Compost (No. 1 or 2) in 4 cm diameter minipots. The test compounds were formulated either by bead milling with aqueous Dispersol T or as a solution in acetone or acetone/ethanol which was diluted to the required concentration immediately before use. For the foliage diseases, the formulations (100 ppm active ingredient) were sprayed on to the foliage and applied to the roots of the plants in the soil. The sprays were applied to maximum retention and the root drenches to a final concentration equivalent to approximately 40 ppm a.i./dry soil. Tween 20, to give a final concentration of 0.05% was added when the sprays were applied to cereals.

For most of the tests the compound was applied to the soil (roots) and to the foliage (by spraying) one or two days before the plants were inoculated with the disease. An exception was the test on *Erysiphe graminis* in which the plants were inoculated 24 hours before the treatment. Foliar pathogens were applied by spray as spore suspensions onto the leaves of test plants. After inoculation, the plants were put into an appropriate environment to allow infection to proceed and then incubated until the disease was ready for assessment. The period between inoculation and assessment varied from four to fourteen days according to the disease and environment.

The disease control was recorded by the following grading:
4=no disease
3=trace—5% of disease on untreated plants
2=6-25% of disease on untreated plants
1=25-59% of disease on untreated plants
0=60-100% of disease on untreated plants
The results are shown in Table II.

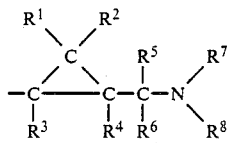
(II)

and the other of X and Y is hydrogen atom, a halogen atom, or an alkyl, alkoxy, cycloalkyl, cycloalkylalkyl, alkynyl, optionally substituted aryl, optionally substituted aralkyl, optionally substituted aralkoxy, optionally substituted aryloxy, or haloalkyl group, or a

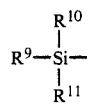

group wherein $R^9$, $R^{10}$ and $R^{11}$ are alkyl, alkenyl, alkynyl, cycloalkyl, cycloalkylalkyl or aryl, Z is a sulphur atom, A and B have the same significance as X or Y excluding a group of formula (II), $R^1$, $R^2$, $R^3$ and $R^4$ each represent a hydrogen atom, a halogen atom or an alkyl group containing from 1 to 4 carbon atoms, $R^5$ and $R^6$ each represent a hydrogen atom or an alkyl group containing from 1 to 4 carbon atoms and $R^7$ and $R^8$ each represent an alkyl group containing from 1 to 4 carbon atoms or $R^7$ and $R^8$ together with the adjacent nitrogen atom form a heterocyclic ring which may optionally contain an additional hetero atom; and acid addition salts thereof.

2. Compounds having the general formula:

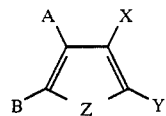
(I)

and stereoisomers thereof, wherein one of X and Y, but not both, is a group of the formula (II):

| COMPOUND NO. | PUCCINIA RECONDITA (WHEAT) | ERYSIPHE GRAMINIS (BARLEY) | VENTURIA INAEQUALIS (APPLES) | CERCOSPORA ARACHIDICOLA (PEANUTS) |
|---|---|---|---|---|
| 1 | 1 | 4 | 1 | 0 |
| 4 | 4 | 4 | 4 | 4 |
| 5 | 1 | 4 | 4 | 2 |
| 6 | 4 | 4 | 0 | 4 |
| 7 | 0 | 4 | 0 | 3 |
| 8 | 0 | 4 | 4 | 0 |
| 9 | 0 | 4 | 4 | 0 |
| 10 | 0 | 3 | 3 | 0 |
| 11 | 0 | 1 | 0 | 0 |
| 12 | 1 | 4 | 4 | 0 |

We claim:
1. Compounds having the general formula:

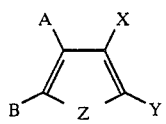
(I)

and stereoisomers thereof, wherein one of X and Y, but not both, is a group of the formula (II):

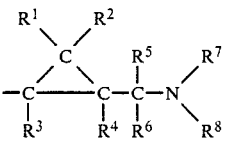
(II)

and the other of X and Y is a hydrogen atom, a halogen atom, or a $C_{1-6}$alkyl, $C_{3-6}$cycloalkyl, $C_{4-7}$cycloalkylalkyl, $C_{2-6}$alkenyl, $C_{2-6}$alkynyl, phenyl, benzyl, $C_{1-6}$alkoxy, phenyloxy, benzyloxy or halo$C_{1-6}$alkyl group, the phenyl, benzyl, phenoxy or benzyloxy being optionally substituted with one or more halogen atoms or $C_{1-6}$alkyl, halo$C_{1-6}$alkyl, $C_{1-6}$alkoxy, halo$C_{1-6}$alkoxy, nitro, phenyl or phenoxy groups, Z is a sulphur atom, A and B have the same significance as X or Y excluding a group of formula (II), $R^1$, $R^2$, $R^3$ and $R^4$ each represent a hydrogen atom, a halogen atom or an alkyl group containing from 1 to 4 carbon atoms, $R^5$ and $R^6$ each represent a hydrogen atom or an alkyl group containing from 1 to 4 carbon atoms, and $R^7$ and $R^8$ each represent an alkyl group containing from 1 to 4 carbon atoms or $R^7$ and $R^9$ together with the adjacent nitrogen atom form a piperidine, morpholine, thiomorpholine, pyrrolidine or piperazine ring optionally substituted with one or more of $C_{1-4}$alkyl, phenyl or hydroxy$C_{1-4}$alkyl; and acid addition salts thereof.

3. Compounds having the general formula:

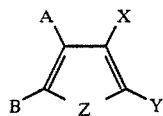

and stereoisomers thereof, wherein Y is a group of the formula (II):

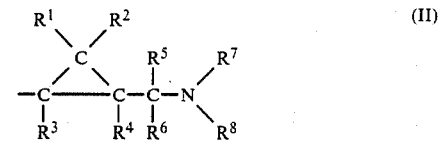

and X is a hydrogen atom; Z is a sulphur atom; A is a hydrogen atom; B is a halogen atom, a $C_{1-4}$alkyl group or a trimethylsilyl group; $R^1$, $R^2$, $R^3$, $R^4$, $R^5$ and $R^6$ each represent a hydrogen atom; and $R^7$ and $R^8$ together with the adjacent nitrogen atom form a piperidine or 2,6-dimethylmorpholine ring; and acid addition salts thereof.

4. The compounds:
4-[2-(5-n-butylthiophen-2-yl)-trans-cyclopropylmethyl]-2,6-cis-dimethylmorpholine,
4-[2-(5-t-butylthiophen-2-yl)-trans-cyclopropylmethyl]-2,6-cis-dimethylmorpholine.

5. The compound of formula:

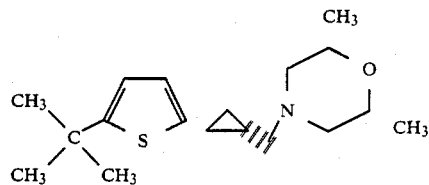

6. A fungicidal composition comprising a compound or salt thereof as claimed in any of claims 1 to 5 and, optionally, a carrier or diluent.

7. A method of combatting fungi which comprises applying to a plant, or seed of a plant, or to the locus of the plant or seed, a compound or salt thereof as claimed in any of claims 1 to 5.

* * * * *